United States Patent
Khursheed (10) Patent No.: US 7,294,834 B2
(45) Date of Patent: Nov. 13, 2007

(54) SCANNING ELECTRON MICROSCOPE (75) Inventor: Anjam Khursheed, Chuville (SG)

(73) Assignee: National University of Singapore, Singapore (SG)

( * ) Notice: Subject to any disclaimer, the term of this patent is extended or adjusted under 35 U.S.C. 154(b) by 197 days.

(21) Appl. No.: 11/155,014

(22) Filed: Jun. 16, 2005

(65) Prior Publication Data

US 2006/0060782 A1   Mar. 23, 2006

Related U.S. Application Data

(60) Provisional application No. 60/579,676, filed on Jun. 16, 2004.

(51) Int. Cl.
*G01N 23/00* (2006.01)
(52) U.S. Cl. .................. 250/310; 250/307; 250/311; 250/396 ML
(58) Field of Classification Search .................. None
See application file for complete search history.

(56) References Cited

U.S. PATENT DOCUMENTS

| 6,774,646 | B1 * | 8/2004 | Han et al. | 324/751 |
| 6,933,501 | B2 * | 8/2005 | Kaji et al. | 250/311 |
| 7,075,075 | B2 * | 7/2006 | Adamec et al. | 250/310 |

OTHER PUBLICATIONS

John T.L. Thong, "Electron Beam Testing Technology," New York, Plenum, 1998.

L. Reimer, "Scanning Electron Microscopy, Physics of Image Formation and Microanalysis, 2nd edition," Chapter 5: Electron Detectors and Spectrometeres, pp. 171-204, 1998.

A. Khursheed, "Aberration Characteristics of Immersion Lenses for LVSEM," Ultramicroscopy, 93, pp. 331-338, 2002.

V.N.E. Robinson, "An Annular Toroidal Backscattered Electron Energy Analyser for use in Scanning Electron Microscope," Scanning, vol. 18, pp. 556-561, 1996.

A. Khursheed, "Recent Developments in Scanning Electron Microscope Design," Advances in Imaging and Electron Physics, vol. 115, edited by P.W. Hawkes, San Diego: Academic Pres.

J.E. Barth and P. Kruit, "Addition of Different Contributions to the Charged Particle Probe Size," Optik, vol. 101(3), pp. 101-109, 1996.

Tromp, R.M., Mankos, M., Reutr, M.C., Ellis, A.W. and Copel, M., "A New Low Energy Electron Microscope," Surface Review and Letters, vol. 5, No. 6 pp. 1189-1197, 1998.

(Continued)

*Primary Examiner*—Jack I. Berman
*Assistant Examiner*—Zia R. Hashmi
(74) *Attorney, Agent, or Firm*—Dinsmore & Shohl LLP (57) ABSTRACT

In a scanning electron microscope, an emitted primary electron beam is diverted by an angle of at least about 45 degrees prior to incidence with a specimen. The beam may be bent by a magnetic separator. The separator may also serve to deflect secondary electron and back scattered electrons. As the angle of emissions and reflections from the specimen is close to the angle of incidence, bending the primary electron beam prior to incidence, allows the electron source to be located so as not to obstruct the travel of emissions and reflections to suitable detectors.

34 Claims, 7 Drawing Sheets

OTHER PUBLICATIONS

L. Reimer, "Transmission Electron Microscopy, Physics of Image Formation and Microanalysis, 4th Edition," Chapter 4.6: Electron Spectrometers and Filter Lenses, pp. 118-120, 1997.

H.C. Kan, T. Dukop and R.J. Phaneuf, J.Vac Sci Technol., B20 (2002) 2519.

Khursheed, A., Yan, Z., Karupiah, N., "Permanent Magnet Objective Lenses for Multi-Column Electron Beam System," Rev. Sci. Instrum., 72(4), pp. 2106-2109.

Khursheed, A. and Osterberg, M., A Spectroscopic Scanning Electron Microscope Design, Scanning vol. 26, (2004), pp. 296-306.

* cited by examiner

SCANNING ELECTRON MICROSCOPE

CROSS-REFERENCE TO RELATED APPLICATIONS

This application claims benefits from U.S. Provisional Patent Application No. 60/579,676 filed Jun. 16, 2004, the contents of which are hereby incorporated herein by reference.

FIELD OF THE INVENTION

The present invention relates generally to scanning electron microscopes (SEMs), and more particularly to SEMs in which a primary electron beam is deflected prior to incidence with a specimen.

BACKGROUND OF THE INVENTION

Scanning electron microscopes are highly versatile electron beam instruments that can provide images over 100 times more magnified than commercial optical microscopes. They have applications in a wide range of different research areas, including, medicine, biology, material science and microelectronics.

In principle, many analytical techniques can be combined with the normal operation of a SEM, but in practice, they are limited to a few routinely used add-on attachments. The main reason for this lies in the way SEMs are currently designed. At present, conventional SEMs include an electron gun, electromagnetic lenses, scan coils and apertures. The electromagnetic lenses are usually divided into two categories, condenser lenses that are placed immediately after the electron gun, and the objective lens located just before the specimen. Typical SEMs produce a high energy (1-30 keV) beam of electrons that is successively focused into a submicron probe and raster scanned over the sample's surface. This beam of electrons is normally referred to as the primary beam.

Unfortunately, most of the electrons and photons that are scattered back from the sample travel back towards the column and are therefore difficult to detect and analyze. Moreover, the distance between the lower pole-piece of the objective lens and the surface of the sample, commonly called the working distance, is relatively small, typically restricted to be between 3 to 25 mm. The acquisition of high resolution images requires that this distance be minimized: the working distance in many cases needs to be less than 5 mm. There is therefore little room in this design to mount detectors and spectrometers that can efficiently collect the secondary electrons and photons generated by the primary beam-specimen interaction or analyze their energy spectra with high resolution.

The SEM uses secondary electrons to form its most common form of topographic image. Secondary electrons are scattered electrons having energies of only a few eV. The secondary electron detector is placed to one side of the specimen so that it does not influence or obstruct the primary beam. This off-axis position, however, results in poor collection efficiency for the secondary electrons, typically well below 50% in most conventional SEMs.

Another popular mode of imaging in SEMs is to use more elastically scattered electrons known as back scattered electrons (BSEs). BSEs are defined to have energies ranging from 50 eV up to the primary beam energy. In conventional SEMs, BSEs have straight line trajectory paths radiating out in different directions, and a special purpose BSE detector is usually mounted just below the objective lens pole-piece to collect the wide-angle BSEs. The BSE detector usually takes the form of a side-entry attachment having a hole to allow passage of the primary beam. Due to its restricted angle of collection, the transport efficiency of BSEs reaching the detector is generally low, well below 50%. Some BSEs are inevitably detected by the secondary electron detector, creating a background current to the secondary electrons signal and degrading secondary electron contrast information. In general, the mixing of secondary electrons and BSEs is undesirable since BSEs provide poorer spatial resolution than secondary electrons. BSEs however carry stronger material contrast information and, for this reason, their separate detection is preferred.

Other commonly used SEM attachments allow for the detection of X-rays, infrared, UV and visible light radiation. An energy-dispersive X-Ray spectrometer (EDS), or a wavelength dispersive X-Ray spectrometer (WDS), enables the SEM to identify the presence of different metals. The Cathodoluminescence technique (CL) works by detecting infrared, UV or visible light radiation from certain specimens like semi-conductors and some organic materials. The spectrum and transient response of the CL signal can provide useful analytical information about the specimen. Although EDS, WDS or CL attachments are very useful, conventional SEM designs are not optimized for their use, precisely for the same reasons that preclude the high efficiency collection of secondary electrons and BSEs. In order not to obstruct the primary beam, their detectors must be placed to one side of the specimen. Moreover, since the working distance must be kept relatively small, only a small fraction of the total emission angle can be captured.

There are several instances where energy filtering of the scattered electrons provides important analytical information about the sample, however, the difficulty of employing high resolution spectrometers into conventional SEMs is well documented in L. Reimer, Scanning Electron Microscopy, Physics of Image Formation and Microanalysis, $2^{nd}$ edition, chapter 5: Electron Detectors and Spectrometers, pp. 171-204, 1998. The technique of quantitative voltage contrast for instance, functions by monitoring energy shifts in the secondary electron spectra.

Although a variety of different electron/energy detectors have been proposed, no SEM capable of using a variety of detectors has emerged. Instead, special purpose Electron Beam Test (EBT) columns have been built, as for example detailed in John T. L. Thong, *Electron Beam Testing Technology*, New York, Plenum, 1993.

Accordingly, there remains a need for a flexible SEM, capable of detecting various emissions or scatterings from a specimen.

SUMMARY OF THE INVENTION

SEMs that do not restrict detectors or spectrometers to be located in the small space between a conventional SEM objective lens and the specimen are disclosed. These SEMs are predicted to have high transport efficiency for all scattered electrons and photons, from the specimen to their respective detectors.

In accordance with an aspect of the present invention, an emitted primary electron beam in an SEM is diverted by an angle of at least about 45 degrees prior to incidence with a specimen. As the angle of emissions and reflections from the specimen is close to the angle of incidence, bending the primary electron beam prior to incidence allows the electron source to be located so as not to obstruct the travel of emissions and reflections to suitable detectors.

In accordance with an aspect of the present invention, there is provided a method of operating a scanning electron microscope. The method includes generating a primary electron beam; guiding the beam to illuminate a specimen; detecting at least one of photons, scattered electrons, and secondary electrons emitted by the specimen as a result of the illuminating. The guiding includes deflecting said beam by an angle of at least 45 degrees.

In accordance with another aspect of the present invention, there is provided a scanning electron microscope that includes: a plurality of electron sources, each for emitting a primary electron beam; a plurality of deflectors, each for deflecting one of the electron beams by an angle of at least 45 degrees; at least one focusing lens for focusing each of the plurality of beams to illuminate at least one specimen; and a plurality of detectors for detecting at least one of photons, scattered electrons, and secondary electrons emitted by at least one specimen as a result of the plurality of beams illuminating at least one specimen.

In accordance with yet another aspect of the present invention, there is provided a scanning electron microscope includes: an electron source, for emitting a primary electron beam; a deflectors, for deflecting the primary electron beam by an angle of at least 45 degrees; a focusing lens downstream of the deflector for focusing said beam to illuminate the specimen; a plurality of detectors for detecting at least one of photons, scattered electrons, and secondary electrons emitted by at least one specimen as a result of the plurality of beams illuminating at least one specimen.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures which illustrate by way of example only, embodiments of the present invention.

DETAILED DESCRIPTION

Figure 1:
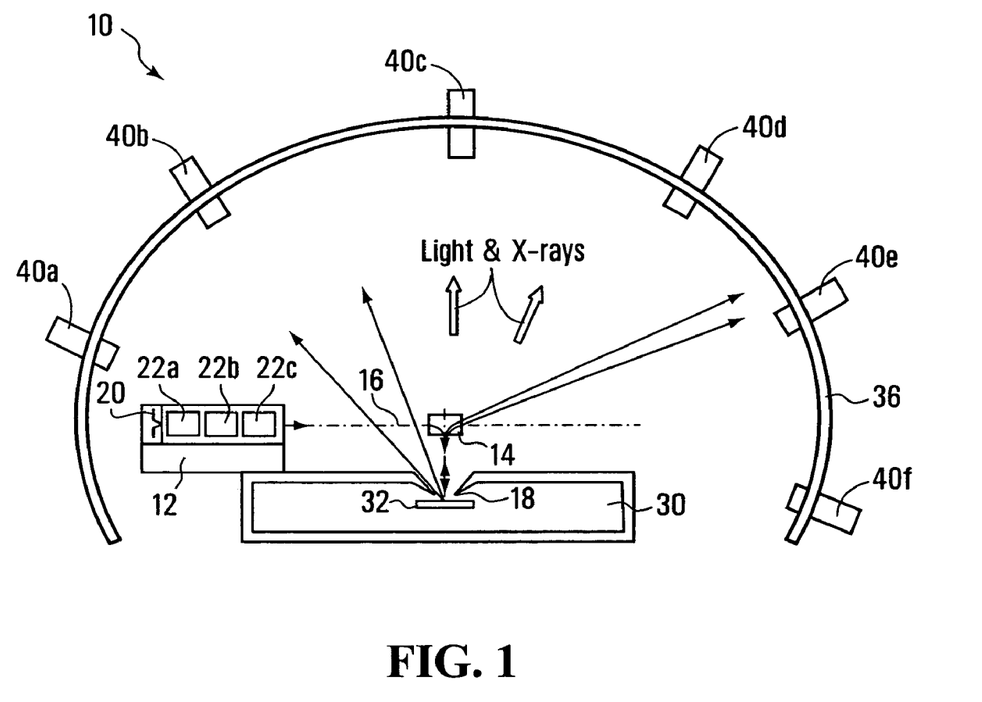
FIG. 1 is a simplified schematic diagram of an SEM exemplary of an embodiment of the present invention.

SEM 10, exemplary of an embodiment of the present invention, is schematically depicted in FIG. 1. SEM 10 includes an SEM column 12, placed on its side, and a magnetic separator 14. Magnetic separator 14 guides an electron beam 16 emitted by SEM column 12, to change its direction of travel from generally horizontal to generally vertical. A primary electron beam 16 is directed by magnetic separator 14, through an objective lens 18 onto a specimen 32. In the depicted embodiment objective lens 18 forms part of a combined collection chamber/objective lens 30.

SEM column 12 includes conventional SEM components, and includes an electron gun 20, a series of electromagnetic lenses 22a, 22b, 22c (collectively lenses 22), scanning coils, stigmators, (not specifically illustrated) and the like. However, final lens 22c is no longer the objective lens of the microscope. Instead, the final lens 22c of SEM column 12 is used as an auxiliary lens whose main purpose is to focus beam 16 onto magnetic separator 14. Final lens 22c has a focal length that is longer than the final lens of a conventional SEM. Apart from this difference, the horizontal SEM column 12 may be the same as a conventional SEM column. There may be a need to provide for stigmatic corrections after the primary beam is deflected. If required, this can easily be achieved by placing small quadrupole units just above the specimen chamber integrated objective lens 30.

Example objective lenses suitable for use as objective lens 18 in SEM 10 are known as mixed field retarding immersion lenses. These types of lenses involve immersing the specimen in strong to moderate electric and magnetic fields. Their high resolution characteristics have been, for example, observed in A. Khursheed, Aberration characteristics of immersion lenses for LVSEM, *Ultramicroscopy*, 93, pp 331-338, 2002.

A plurality of electron and photon detectors 40a, 40b . . . 40f (individually and collectively detectors 40) are mounted at hemispherical region 36, essentially unrestricted by space constraints. Each detector 40 may be positioned at a different location in this hemispherical region, and a different angle relative to the angle of incidence of beam 16 on specimen 32. Optionally, detectors 40 may be located at different radial positions, provided that detectors at more inwardly radial positions do not materially obstruct multiple detectors located at more distant radial positions.

Detectors 40 take the form of a variety of suitable electron detectors or spectrometers, known in the art. Conveniently, each detector 40 may be suitable for specifically detecting electrons of a specific type, or energy or photons. This allows for improved collection efficiency and higher energy resolution spectroscopy of the scattered electrons and photons than presently possible with conventional SEMs. Example detectors suitable for use as detectors 40 include wide angle BSE and Auger electron detectors, retarding field magnetic sector spectrometers, and the like. A wide variety of other spectrometers, including those that collect electrons over the full $2\pi$ range in the azimuthal direction, as for example detailed in Rau and V. N. E. Robinson, An annular toroidal backscattered electron energy analyser for use in the scanning electron microscope, *Scanning*, Vol. 18, pp. 556-561, 1996 may similarly be used as detectors 40. Of course detectors 40 need not be magnetic.

In operation, primary electron beam 16 emitted by column 12 is emitted along a generally horizontal axis and strikes a specimen 32 along a generally vertical incident axis. Specimen 32 is located inside or just above the objective lens 18, which is integrated as part of collection chamber/objective lens 30. Within collection chamber/objective lens 30, specimen 32 is biased to a suitable negative potential. In the example embodiment, specimen 32 is biased to about −5 kV. This helps collimate the scattered electrons, gives the scattered electrons close to the axis of incidence of beam 16 enough kinetic energy to be deflected side-ways by the magnetic separator 14, and provides high spatial resolution on the primary beam 16 as it strikes specimen 32.

Magnetic separator 14 creates a magnetic field directed into the plane shown in FIG. 1, thereby causing primary beam 16 to bend and trace out part of a generally circular (i.e. round) trajectory, as it travels from column 12 to specimen 32.

Upon impact of beam 16 on specimen 32, electrons are back scattered, and photons and secondary electrons may be emitted, in a direction away from specimen 32. As column 12 is located laterally away from specimen 32, and beam 16 has been bent prior to incidence, scattered and emitted electrons and photons are therefore not obstructed by the SEM column 12 which lies in a horizontal direction located well away from sample 32. The scattered and emitted electrons and photons are directed on to detectors 40 above specimen 32, unobstructed by the SEM column 12.

Most of the scattered and emitted electrons are redirected by magnetic separator 14, on to detectors 40. Conveniently, magnetic separator separates the secondary electrons based on their energies, deflecting secondary electrons of differing energies by corresponding different angles. Detectors 40 through emitted photons, scattered and emitted electrons thus image specimen 32. To image the entire specimen, beam 16 is raster scanned across specimen 32, under control scanning plates forming part of column 12.

Additionally, or alternatively, the well known technique of scanning Auger spectroscopy (SAM) may be used in SEM 10, by incorporating detectors 40 capable of detecting Auger electrons. Auger electrons emanate from the inner shell of atoms in the sample and are emitted from a very thin layer (<2 nm) below the sample's surface. Auger electron energies typically range from 20 to 2000 eV. By analyzing characteristic peaks in their energy spectrum, different elements on the surface of specimen 32 can be identified.

Figure 2A:
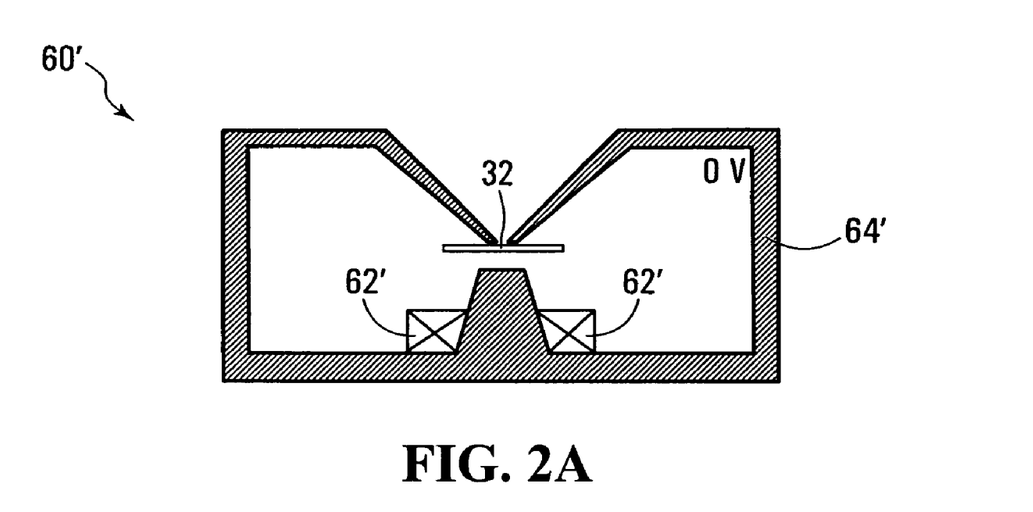
FIGS. 2A and 2B are simplified cross-sectional diagrams of objective lenses that may be used in the SEM of FIG. 1.
Figure 2B:
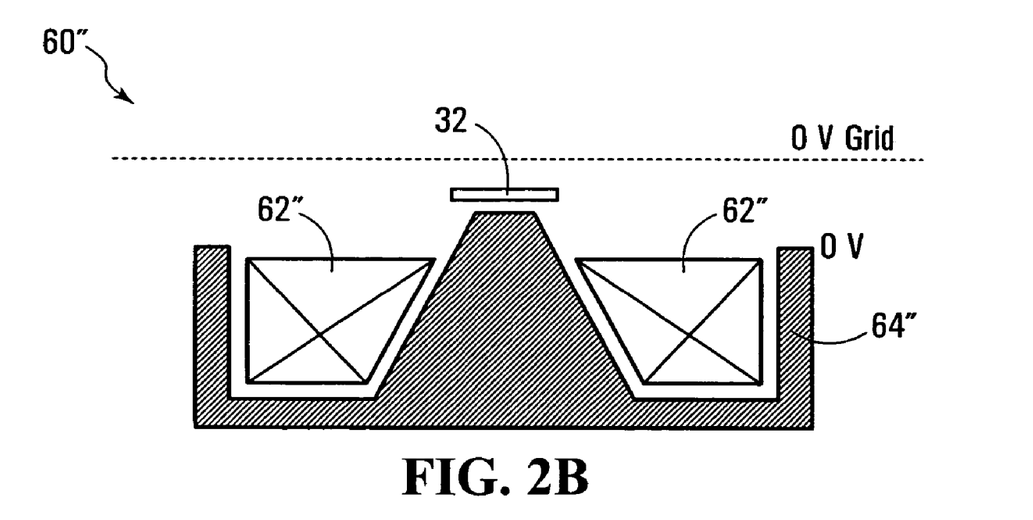

Two lenses 60' and 60" useable as collection chamber/objective lens 30 are shown in FIGS. 2A and 2B, respectively. Lenses 60' and 60" include iron circuits 64' and 64" and energizing coils 62' and 62". A person of ordinary skill will recognize that lens 60' is a full immersion lens, while lens 60" is a single pole lens. Lenses 60' and 60" can separate low energy scattered electrons from Auger electrons and BSEs. This is because the scattered electrons experience a sharply decreasing magnetic field as they travel away from the specimen. The collimating effect strongly depends on the initial energies of the scattered electrons: the low energy electrons, such as the secondary electrons, are confined to a much smaller area around the primary beam axis than Auger electrons, which are in turn closer to the axis than BSEs.

Simulation illustrates low landing energies on specimen 32 can be achieved by adjusting the voltage of primary beam 16 to be close to the voltage of specimen 32. Here SEM 10 can operate in the low voltage SEM mode, commonly known as LVSEM, as for example detailed in Khursheed A., Recent Developments in Scanning Electron Microscope Design, *Advances in Imaging and Electron Physics*, Vol. 115, edited by P. W. Hawkes, San Diego: Academic Press, pp. 197-285, 2001. To focus primary beam 16 on to the specimen, an excitation strength of 1185 AT may be used. The predicted focal length f, spherical aberration coefficient, $C_s$, and chromatic aberration coefficient, $C_c$ for these conditions are: f=0.697 mm, $C_s$=0.231 and $C_c$=0.214 mm. The electric field strength at the sample is less than 2.5 kV/mm, a fairly moderate value. Taking 0.4 eV to be the energy spread for a thermal field emission (TFE) gun, the Bath-Kruit root-sum formula, as for example detailed in J. E. Bath and P. Kruit, "Addition of different contributions to the charged particle probe size", *Optik*, Vol. 101 (3), p 101-9, (1996) predicts the minimum primary beam diameter at the specimen to be 1.14 nm. This prediction is close to the theoretical limit for immersion lenses. Within the class of LVSEM objective lenses, this type of mixed field retarding lens has the lowest on-axis aberration coefficients.

For Auger electron detection, landing energies of around 3 keV are preferred, with a primary beam energy of about 8 keV. For these conditions, the focal length and on-axis aberrations are also predicted to be low: f=0.851 mm, $C_s$=0.441 mm and $C_c$=0.423 mm. An excitation of 1533 AT focuses the primary beam on to the specimen. The predicted minimum primary beam diameter at the specimen in this case is 0.784 nm for a TFE gun. The resolution of images for scanning auger microscopy (SAM) typically is usually around 1 μm, recent improvements have reduced it down to around 10 nm. The theoretical resolution predicted for an objective lens suitable for use as objective lens 18 in SEM 10 is significantly better than this, but practical considerations such as the interaction volume and signal-to-noise ratio will be important.

For higher landing energies, an objective lens suitable for use as objective lens 18 in SEM 10 is also predicted to provide greater spatial resolution than conventional SEMs. At a landing energy of 15 keV, the simulated focal length and on-axis aberrations are: f=1.12 mm, $C_s$=0.773 and $C_c$=0.728 mm, yielding a predicted probe diameter of 0.444 nm at the specimen for a TFE gun. These aberration coefficients are typically more than an order of magnitude lower than those for conventional SEMs under similar operating conditions. At 15 keV, the spatial resolution of the SEM is dominated by the interaction volume, and not limited by primary beam optics. However, since SEM 10 allows for the possibility of collecting the more elastic backscattered electrons, a significant improvement in the spatial resolution is expected.

Figure 3:
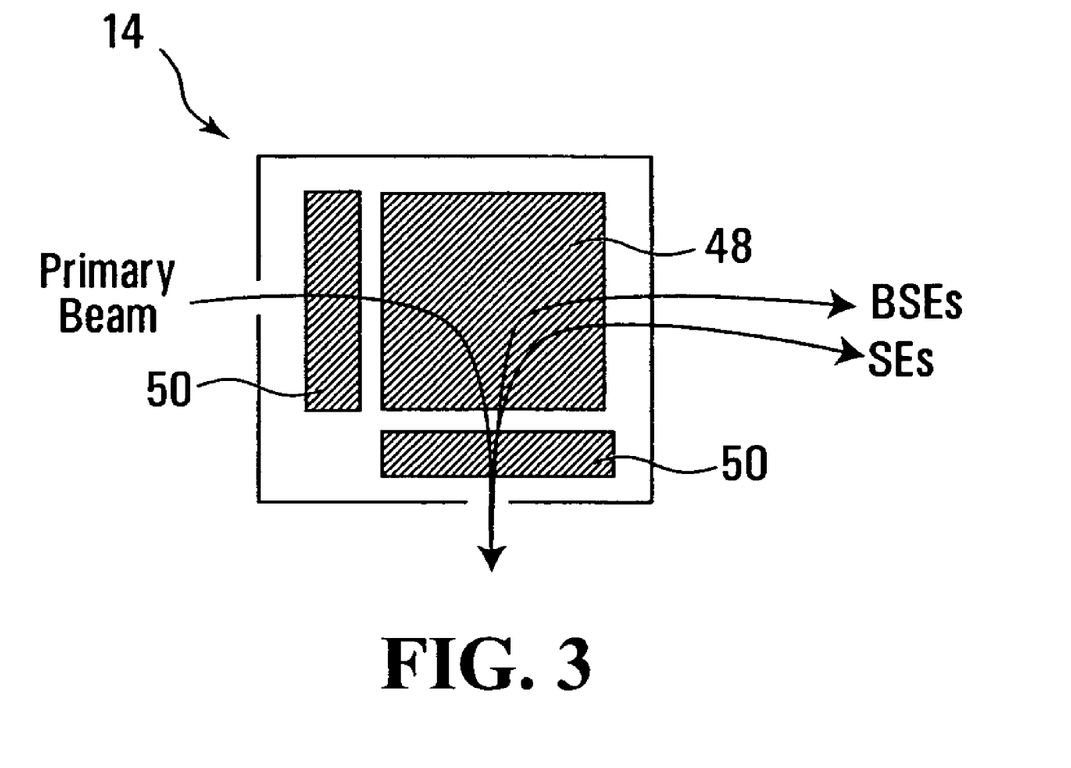
FIG. 3 is a simplified schematic diagram of a magnetic separator of the SEM of FIG. 1.

An example magnetic separator 14 is schematically depicted in FIG. 3. Sector plate 48 and accompanying pre-focusing and post-focusing plates 50 lie in a plane. Identical sector plate and pre-focusing and post-focusing plates lie in a parallel plane opposite plates 48, 50 and spaced therefrom. Plates 48 are designed to deflect the primary beam through an angle of about 90 degrees. Plates 48 are excited separately from plates 50.

Conveniently, the presence of pre-focusing plates and post-focusing plates 50, allows separator 14 to act as a round lens that may focus primary beam 16 (while maintaining a circular trajectory). That is, the beam is bent through an angle without distortion. When the path of the primary beam is bent through 90 degrees beam, severe distortions on its shape (cross-sectional shape) are typically experienced. However, they can be compensated for by using pre- and post-focusing plates so as depicted in FIG. 3. An example lens is detailed in Tromp R. M., Mankos M., Reuter M. C., Ellis A. W., and Copel M., "A new low energy electron microscope", *Surface Review and Letters*, Vol. 5, No. 6, pp. 1189-1197, (1998).

Suitable parallel separator plates 48 are commonly used in electron optics instrumentation for electron beam deflection and energy spectroscopy, and are more particularly detailed in L. Reimer, Transmission Electron Microscopy, Physics of Image Formation and Microanalysis, 4$^{th}$ edition, chapter 4.6: Electron Spectrometers and Filter Lenses, pp. 118-120, 1997.

All Sector plates 48, 50 are excited by current carrying coils wound on iron rods that are connected to a common iron frame.

If a plane is defined to be parallel to sector plates 48, then out-of-plane focusing is provided for by fringe fields at the edges of the sector plates 48. Fringe fields at the edges of sector plates 48 may play a significant role in focusing the primary beam in the direction perpendicular to its trajectory path. This effect is known as "double-stigmatic focusing", as detailed in L. Reimer, Transmission Electron Microscopy, Physics of Image Formation and Microanalysis, 4$^{th}$ edition, chapter 4.6: Electron Spectrometers and Filter Lenses, pp. 118-120, 1997.

Figure 4:
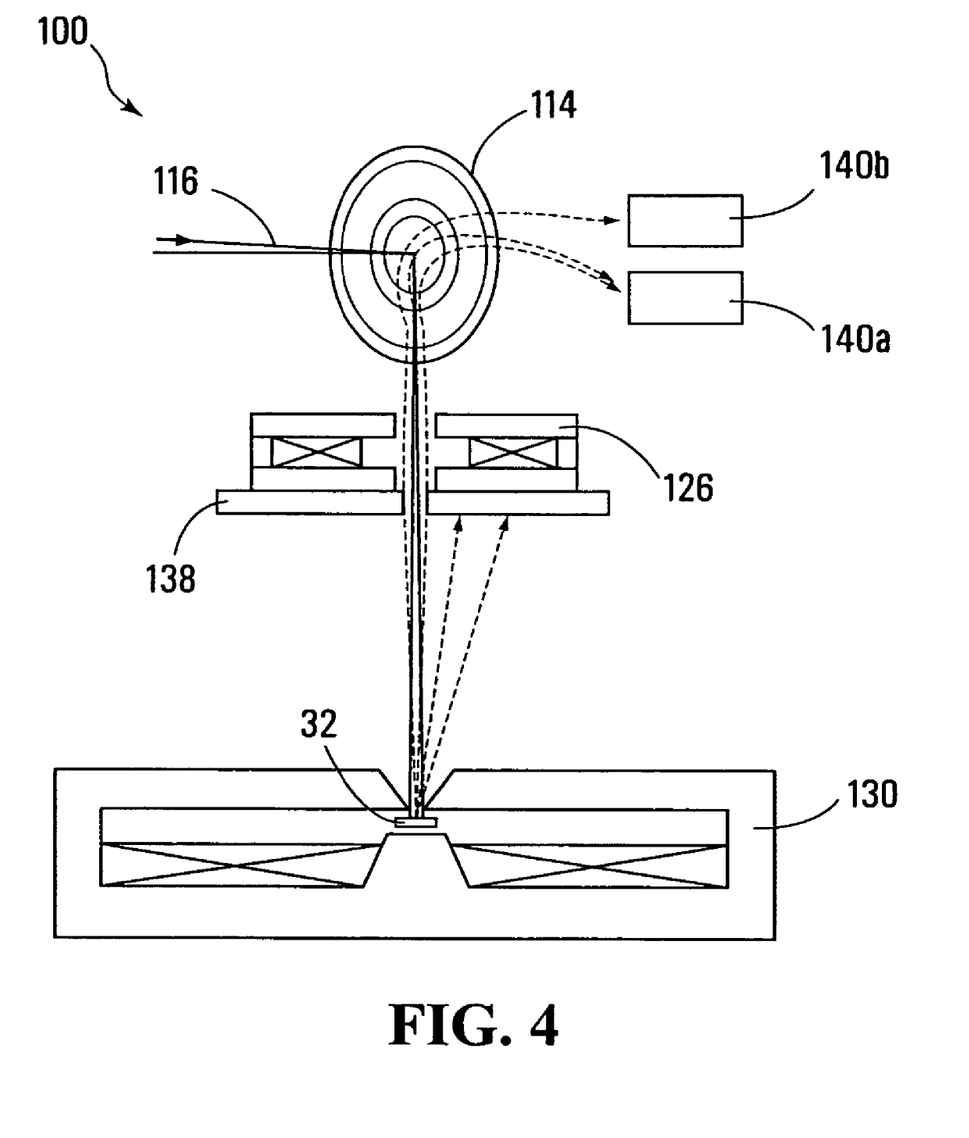
FIGS. 4 and 5 are simplified schematic diagrams of an SEM exemplary of another embodiment of the present invention.
Figure 5:
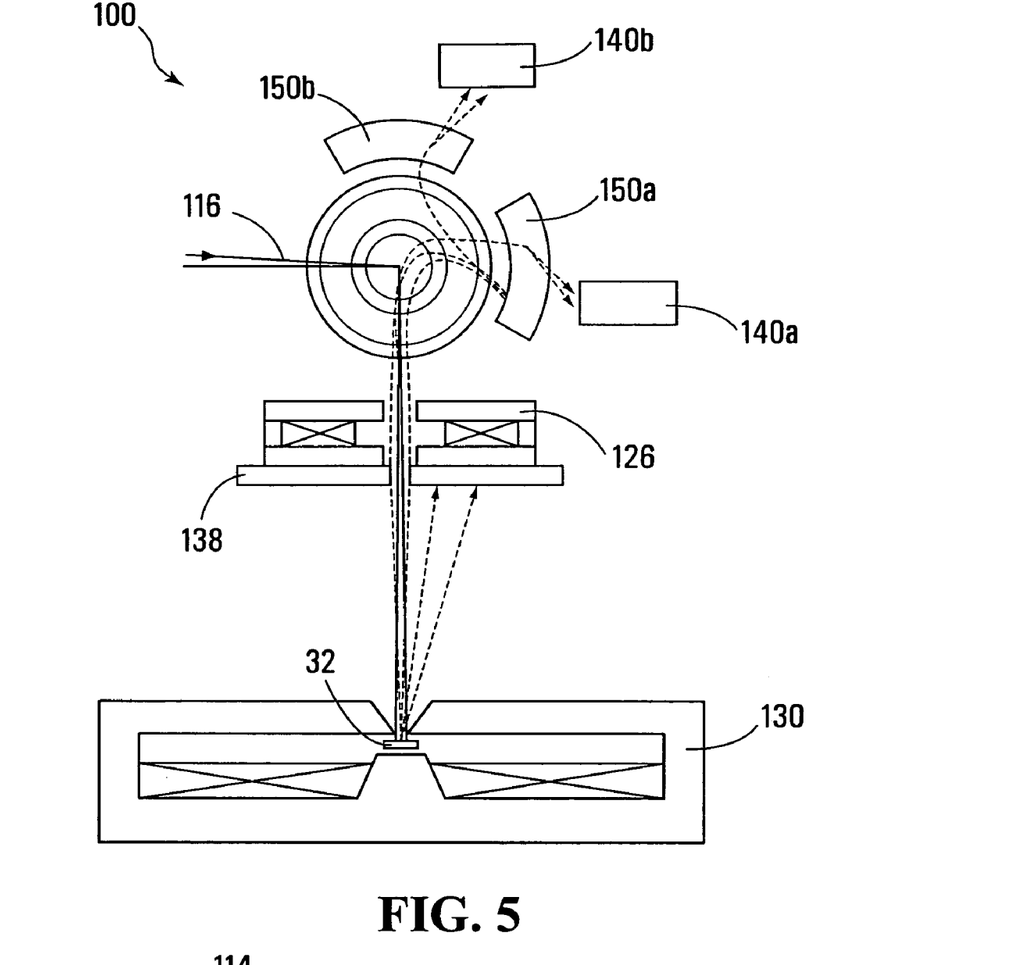
Figure 6:
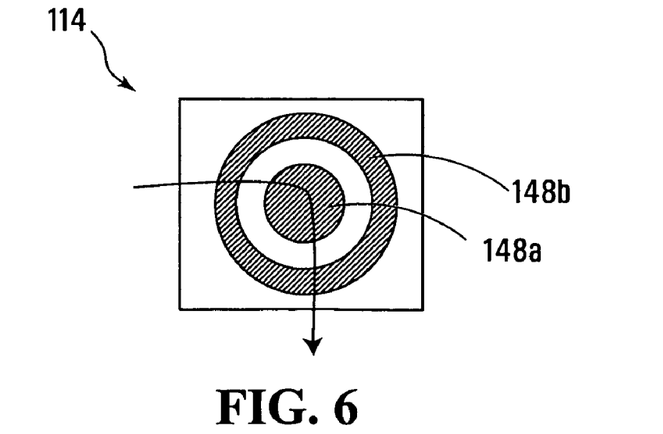
FIG. 6 is a simplified schematic diagram of a magnetic separator of the SEM of FIGS. 4 and 5.

Another SEM 100, exemplary of a further embodiment is illustrated in FIGS. 4 to 6. SEM 100 includes a generally horizontal SEM column (not shown), like column 12 (FIG. 1) capable of emitting primary electron beam 116. A magnetic separator 114 that is generally circular in shape deflects primary beam 116 by angles other than 90 degrees.

An example magnetic separator 114 is further illustrated in FIG. 6. As illustrated, example magnetic separator 114 includes two pairs of parallel plates 148a and 148b. One pair of plates 148a and 148b lie within the same plane. The other pair (not specifically shown) lie in another plane, directly opposite and spaced from plates 148a and 148b. Parallel plates 148a are formed as circular plates. Each parallel plate 148b is formed as a concentric ring about a plate 148a, in the plane of a plate 148a. Voltages applied across plates 148a and across plates 148b are independent. By controlling the relative applied voltages, the deflection angle of separator 114 may be controlled to deflect the primary beam through an arbitrary angle. Conveniently, unlike separator 14, electrons always enter and exit normal to the edge of plates 148a and 148b, minimizing aberrations resulting from deflection. For example, the angle of incidence of beam 116 may be deflected between about 45 and 90 degrees (e.g. 60 degrees). An example magnetic separator useable as separator 114 is detailed in H.-C. Kan, T. Durkop and R. J. Phaneuf, J. Vac. Sci. Technol. B 20 (2002) 2519. Additionally, primary beam 116 is focused into the centre of the magnetic separator 114, by the final lens of the column emitting beam 116, causing primary electrons within beam 116 incident on separator 114 at different angles to diverge as they emerge from the magnetic separator 114. An additional transfer lens 126 may correct this, to re-converge beam 116 after deflection as it approaches collection chamber/objective lens 130. This reduces the aberrations of primary beam 116.

As illustrated in FIGS. 4 and 5, a backscatter detector 138 is placed just below transfer lens 126, to detect wide-angle backscattered electrons. As in SEM 10, narrow backscattered electrons and secondary electrons may be deflected by magnetic separator 114, and subsequently collected by detectors 140a and 140b, suited specifically for the detection of backscattered electrons and secondary electrons, respectively. As wider-angle scattered electrons are collected by detector 138, the scattered electrons that now are deflected by separator 114 have a much smaller angular range than in SEM 10 and are not as dispersed as in SEM 10. Thus, only one or two detectors 140a and 140b may be sufficient.

Optionally, SEM 100 may further include two additional retarding field sector magnets 150a and 150b placed between separator 114 and detectors 140a and 140b, as illustrated in FIG. 5. Field sector magnets 150a and 150b assist in obtaining high resolution spectra of the BSEs and secondary electrons, respectively.

The voltage and magnetic field strengths of the BSE retarding field sector magnet 150a may be adjusted to values $V_{f1}$ and $B_{f1}$ respectively. $V_{f1}$ is set to be at a negative voltage close the voltage of beam 116, thus acting as a mirror for the secondary electrons (which have a lower kinetic energy), while transmitting backscattered electrons through to the BSE detector 140a. BSE detector 140a is a multi-channel detector, directly capturing the spectrum. In this way, a high resolution BSE spectra will be detected from the transmitted BSEs, whose energy resolution is enhanced by the retarding action of the sector. The SE retarding field sector magnet 150b, in like manner to the BSE sector magnet 150a, is able to produce a high resolution SE spectrum. A retarding field voltage $V_{f2}$ and sector magnetic field strength of $B_{f2}$ are applied to magnet 150b. Detector 140b can also detect the spectra of Auger electrons. The maximum energy detected by the SE detector 140b will be set by $V_{f1}$ on the BSE sector magnet 150a, which can be adjusted to acquire the higher energy Auger electrons as well as the lower energy secondary electrons.

Figure 7:
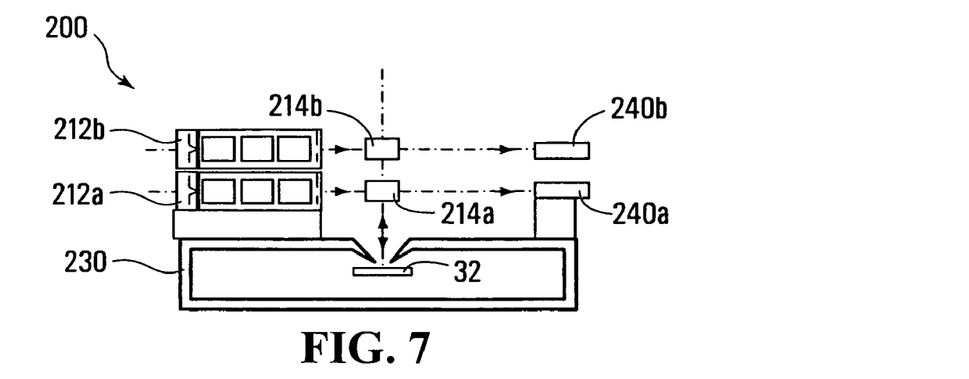
FIG. 7 is a simplified schematic diagram of another SEM, exemplary of an embodiment of the present invention.

SEM 10 may also be modified as illustrated in FIG. 7, to form SEM 200 including multiple SEM columns 212a, 212b (like column 12) arranged one above the other. For simplicity, it is assumed that a plurality of electron detectors 240 (like detectors 40) detect secondary electrons only, and can filter out all incoming Auger electrons or BSEs. Use of secondary electrons is better suited to multi-column SEM 200 since simulation predicts that they can be directed on to a detector 240 located far from the primary beam axis with millimeter precision.

Now, SEM columns 212 may be time-multiplexed, alternating in operation. The two SEM columns 212a and 212b, along with their magnetic separators 214a, 214b and detectors 240a, 240b are aligned with each other and placed at different heights. Each of magnetic separators 214a, 214b may be formed with circular sector plates (like magnetic separator 114), or generally square or rectangular sector plates (like magnetic separator 14). The focal length of the objective lens 230 (formed as an immersion lens, like lens 60') is pulsed, for example by varying the potential of the specimen 32, in such a way so as to focus the image formed by each column from specimen 32 at different time intervals. Time-multiplexing illumination of one specimen using multiple SEM columns 212a and 212b may be desirable in numerous situations. One situation is the need to observe a large field of view while imaging a very small part of the specimen. An extra column in this instance greatly assists in specimen navigation at high magnification: one column 212a is used in high resolution mode, while the other column 212b is used in low resolution mode. Another example may help in the neutralization of charge build-up on dielectric surfaces. Here, two SEM columns 212a and 212b typically operate at different primary beam energies in such a way that while one column creates positive charge at the specimen, the second column neutralizes it.

Magnetic separators 214 may further be encased so as to filter electrons within a certain energy range, so as to only pass secondary electrons while filtering other electrons. Such casing/filtering may limit the energy range of SEM 200, but would allow for multi-column operation with limited interference of secondary electrons attributable to each column.

Figure 8A:
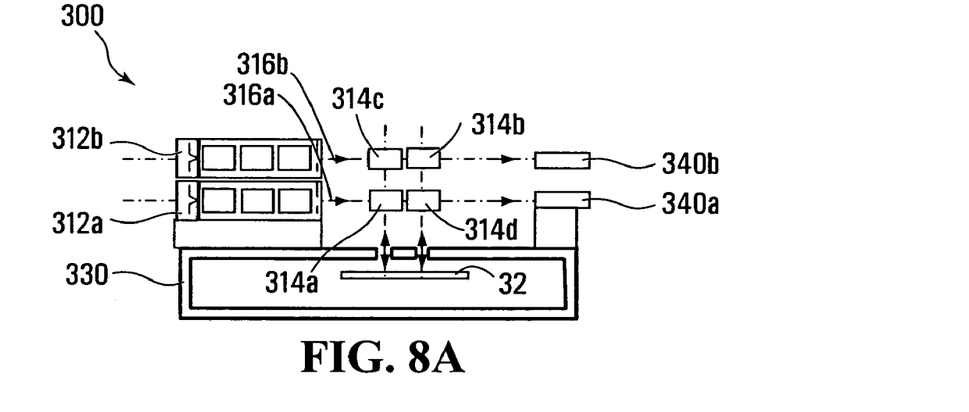
FIG. 8A is a simplified schematic diagram of another SEM, exemplary of an embodiment of the present invention.
Figure 8B:
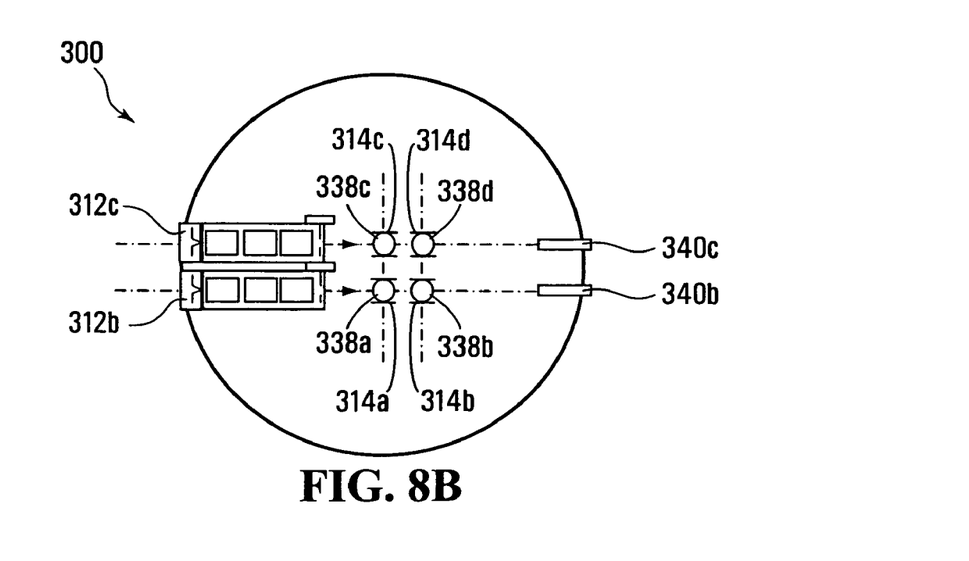
FIG. 8B is a simplified top plan view of FIG. 8A.

Another multi-column SEM 300, exemplary of yet another embodiment of the present invention is illustrated in FIGS. 8A and 8B. As illustrated, SEM 300 includes a two-dimensional array of SEM columns 312 (like columns 212), where different columns illuminate different areas on the same specimen 32. Combined lens/chamber 330, also formed as an immersion lens, includes multiple bores 338a, 338b... (individually and collectively bores 338) arranged in a two dimensional array, above specimen 32. The same arrangement can of course be used on multiple different specimens, placed close together. Each column 312 is associated with a corresponding magnetic separator 314 and a detector 340. Each magnetic separator 314 is aligned with the axis of primary electron beam of one column 312, above a bore 338 of lens/chamber 330.

Again, each of magnetic separators 314 may be formed with circular sector plates (like magnetic separator 114), or generally square or rectangular sector plates (like magnetic separator 14). The primary beam 316 of each column 312 is deflected by a corresponding magnetic separator 314 to enter one bore 338 of lens/chamber 330. Magnetic separators 314 may also further be encased so as to filter electrons within a certain energy range, as described with reference to magnetic separators 214.

Columns 312 are arranged in such a way that the primary and secondary beams of each column 312 do not interfere with the primary and secondary beams of another column. Magnetic separator 314a shown in FIG. 8A for instance, deflects the primary beam of column 312a through bore 338a, which lies below the primary beam that travels through magnetic separators 314b and bore 338b of lens/chamber 330. Likewise, the primary beam that travels through magnetic separators 314c and bore 338c is separate from the primary beam that travels through magnetic separators 314d and bore 338d of lens 360.

A plurality of electron detectors 340 may be located opposite columns 312 to capture secondary and emitted electrons.

Each magnetic separator 314 may similarly deflect secondary electrons and BSEs emitted through a respective bore 338, to guide such electrons onto an electron detector 340.

An example of a multi-bore array objective lens suitable for use as lens/chamber 330 in SEM 300 is more particularly detailed in Khursheed A., Yan Z., and Karuppiah N., Permanent magnet objective lenses for multi-column electron beam systems, *Rev. Sci. Instrum.*, 72 (4), pp. 2106-2109, (2001).

Figure 9:
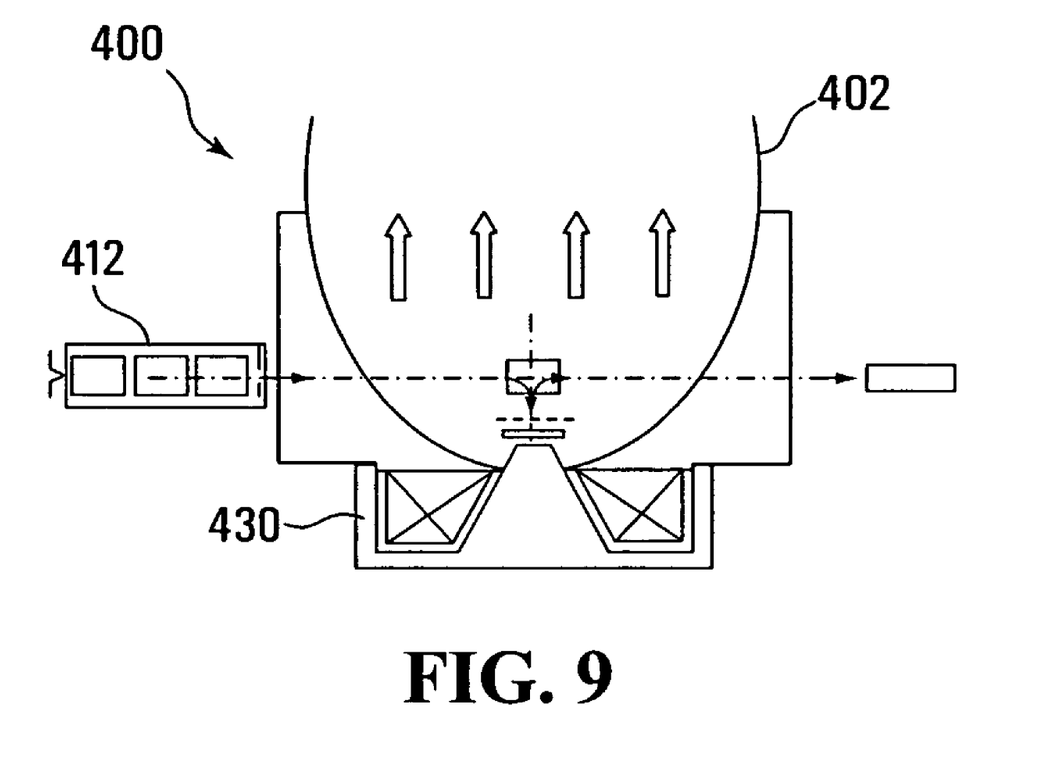
FIG. 9 is a simplified schematic diagram of another SEM exemplary of an embodiment of the present invention.

There are many ways in which the SEM design exemplary of embodiments of the present invention, can combine high efficiency X-ray or CL detection with high efficiency electron detection. One simple approach is to make all detectors 40 (FIG. 1) retractable, so that X-ray/CL detectors can function simultaneously with the detection of the secondary electron image. FIG. 9 shows such an SEM 400 optimized for CL detection. In this case, a single pole objective lens 430 (such as lens 60" in FIG. 2B) may be used to impose less of an obstruction to emitted light from specimen 32 than a full immersion lens. There will of course be some loss in transmission of scattered photons through the 0 volt grid above the specimen, but this can be kept relatively small, typically less than 20%. Instead of using an optical lens beyond the hemispherical collection surface to make photons travel in a parallel direction, a parabolic curved reflective surface 402 can be placed above the single pole objective lens 430, as shown in FIG. 9.

In order to make SEMs disclosed herein more portable, permanent magnet lenses may be used instead of excited electric lenses. For example, in SEM 10 of FIG. 1, a permanent magnet may form part of SEM column 12. Optionally, a weak magnetic or electrostatic lens can be used at the end of this column for focal point adjustments. A permanent magnet may similarly excite objective lens 18. Coarse focusing of primary beam 16 on to the specimen may then be achieved through height movement of specimen 32, and fine focusing may be achieved through varying the potential of specimen 32. The magnetic separators 14 may be mounted into a small iron box that has holes to allow the passage of the primary and secondary beams. By using permanent magnets, the whole arrangement can made small, typically measuring 6 to 8 cm in diameter.

As should now be appreciated, exemplary SEMs are predicted to have high transport efficiency for all scattered electrons and photons, from the specimen to their respective detectors. The transport efficiency for secondary electrons is expected to be around 100% and over 80% for Auger electrons, BSEs and all emitted photons. Secondly, the energies of the scattered electrons can be analyzed with high precision, where the energy resolution, defined as the ratio of energy spread $\Delta E$ to the pass energy E, is expected to be typically better than $10^{-4}$. Thirdly, the new design provides for better separation between secondary electrons, Augers, and BSEs than presently possible. Fourthly, exemplary SEMs (like SEM 100) can easily be extended to incorporate time multiplexed columns and multi-column arrays.

All documents referred to herein, are hereby incorporated by reference herein.

Of course, the above described embodiments and examples are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

What is claimed is:

1. A method of operating a scanning electron microscope, comprising:
   generating a primary electron beam;
   guiding said beam to illuminate a specimen, said beam incident on said specimen along an incident axis;
   detecting at least one of photons, scattered electrons, and secondary electrons emitted by said specimen as a result of said illuminating, with a plurality of detectors each for detecting a specific type of particles that are of a specific energy range;
   wherein the source of said beam is located sufficiently away from said incident axis so as not to obstruct said plurality of detectors, and said guiding comprises deflecting said beam by an angle of at least 45 degrees to allow incidence of said beam on said specimen along said incident axis.

2. The method of claim 1, further comprising raster scanning said primary electron beam over said specimen to illuminate said specimen.

3. The method of claim 2, wherein said guiding comprises bending said beam by about 90 degrees.

4. The method of claim 2, wherein said guiding comprises bending said beam by about 60 degrees.

5. The method of claim 2, wherein said guiding comprises generating a magnetic field acting on said primary electron beam to deflect said beam.

6. The method of claim 1, wherein said detecting comprises detecting secondary electrons at a plurality of locations, said locations at angles varying relative to an angle of incidence of said beam on said specimen.

7. The method of claim 6, further comprising detecting back scattered electrons at a further plurality of locations.

8. The method of claim 6, further comprising detecting Auger electrons at a further plurality of locations.

9. The method of claim 2, wherein said primary electron beam initially has a generally horizontal trajectory.

10. The method of claim 2, further comprising biasing said specimen.

11. The method of claim 2, wherein said guiding is performed by a magnetic separator.

12. The method of claim 11, wherein said magnetic separator comprises two sets of two parallel sector plates.

13. The method of claim 2, wherein said primary beam has a potential proximate a potential of said specimen.

14. The method of claim 11, wherein said magnetic separator comprises two sets of generally round parallel plates to deflect said primary beam by angles other than 90 degrees.

15. The method of claim 14, wherein each of said two sets of generally round plates comprises a generally circular plate, surrounded by a generally circular ring.

16. The method of claim 14, further comprising interposing a retarding field sector magnet between said magnetic separator and one of said detectors.

17. A scanning electron microscope comprising:
a plurality of electron sources, each for emitting a primary electron beam;
a plurality of deflectors, each for deflecting one of said beams by an angle of at least 45 degrees;
at least one focusing lens for focusing each of said beams to illuminate at least one specimen along an incident axis;
a plurality of detectors for detecting at least one of photons, scattered electrons, and secondary electrons emitted by said at least one specimen as a result of said beams illuminating said at least one specimen, each of said detectors for detecting a specific type of particles that are of a specific energy range;
wherein each one of said electron sources is located sufficiently away from said incident axis so as not to obstruct said plurality of detectors, and said deflecting allows incidence of said each beam on said at least one specimen along said incident axis.

18. The microscope of claim 17, wherein said electron sources are arranged to emit said beams in directions parallel to each other.

19. The microscope of claim 18, wherein said electron sources are time multiplexed to sequentially emit said beams.

20. The microscope of claim 17, wherein each of said electron beams is bent by an angle of about 90 degrees as said electron beams pass from said electron sources to illuminate said at least one specimen.

21. The microscope of claim 20, wherein said detectors are arranged on a generally hemispherical surface.

22. The microscope of claim 17, wherein each of said detectors is one of a wide angle back scattered electron detector and an Auger electron detectors.

23. The microscope of claim 17, wherein said plurality of electron sources are arranged to emit said plurality of beams in a two dimensional array.

24. The microscope of claim 17, wherein said electron sources are operable to raster scan said primary electron beams over said at least one specimen.

25. A scanning electron microscope (SEM) comprising:
an electron source, for emitting a primary electron beam;
a deflector, for deflecting said primary electron beam by an angle of at least 45 degrees;
a focusing lens downstream of said deflector for focusing said beam to illuminate a specimen along an incident axis;
a plurality of detectors for detecting at least one of photons, scattered electrons, and secondary electrons emitted by said specimen as a result of said beam illuminating said at least one specimen, each of said detectors for detecting a specific type of particles that are of a specific energy range;
wherein said electron source is located sufficiently away from said incident axis so as not to obstruct said plurality of detectors, and said deflecting allows incidence of said beam on said specimen along said incident axis.

26. The SEM of claim 25, wherein said primary electron beam is raster scanned over said specimen.

27. The SEM of claim 25, wherein said detectors are arranged on a generally hemispherical surface.

28. The SEM of claim 25, wherein one of said detectors is one of a back scattered electron detector and Auger electron detectors.

29. The SEM of claim 25, wherein said deflector comprises a magnetic separator.

30. The SEM of claim 29, wherein said magnetic separator comprises two parallel sector plates.

31. The SEM of claim 30, wherein said sector plates are generally rectangular.

32. The SEM of claim 29, wherein said magnetic separator comprises two generally round parallel plates to deflect said primary beam by angles other than 90 degrees.

33. The SEM of claim 32, further comprising a retarding field sector magnet between said magnetic separator and one of said detectors.

34. The SEM of claim 33, wherein a time varying magnetic field is applied to said field sector magnet.

* * * * *